United States Patent [19]

Achari et al.

[11] 4,225,559
[45] Sep. 30, 1980

[54] CERAMIC ELEMENT SENSOR

[75] Inventors: Achyuta Achari, Detroit; Elmer T. Heiney, III, Huntington Woods, both of Mich.

[73] Assignee: Ford Motor Company, Dearborn, Mich.

[21] Appl. No.: 5,425

[22] Filed: Jan. 22, 1979

[51] Int. Cl.³ ............................................. G01N 27/12
[52] U.S. Cl. ..................................... 422/98; 23/232 E; 60/276; 204/195 S; 252/472; 252/477 R; 324/71 SN; 338/22 S
[58] Field of Search ............................ 252/472, 477 R; 23/232 E; 422/119, 44–48; 60/276; 204/195 S; 338/22 SD; 324/71 SN

[56] References Cited

U.S. PATENT DOCUMENTS

| | | | |
|---|---|---|---|
| 2,782,103 | 2/1957 | Plentiss | 422/98 |
| 4,036,592 | 7/1977 | Broun et al. | 422/96 |
| 4,058,485 | 11/1977 | Chering | 252/477 R |
| 4,066,413 | 1/1978 | Segawa et al. | 422/98 |
| 4,099,922 | 7/1978 | Yasuda et al. | 422/95 |

Primary Examiner—Michael S. Marcus
Attorney, Agent, or Firm—Robert W. Brown; Clifford L. Sadler

[57] ABSTRACT

An improved sensor having a ceramic element that undergoes a change in an electrical characteristic in response to a change in the partial pressure of oxygen in a mixture of gases to which the ceramic element is exposed. Sensors of this type are used to detect the air-fuel ratio of mixtures supplied to internal combustion engines. Prior art titania and zirconia sensors are characterized by little change in their respective electrical characteristics at operating temperatures below about 350° C. A charge transfer material, platinum, has been applied to the ceramic element to facilitate or make possible the electron transfers required for sensor operation. Loss of the platinum charge transfer material by vaporization, as the result of operation at normal elevated temperatures, has been discovered to be the cause of a loss of sensor response at low sensor operating temperatures. The improved sensor has a charge transfer material comprised of an alloy of platinum and rhodium. This alloy, which preferably is 90% platinum and 10% rhodium, reduces the minimum temperature of operation for the sensor and substantially eliminates the aforementioned vaporization loss of the charge transfer material.

5 Claims, 18 Drawing Figures

FIG. 6 TiO₂ THERMISTOR (700x)

FIG. 5 TiO₂ SENSOR (700x)

CERAMIC ELEMENT SENSOR

CROSS-REFERENCE TO RELATED APPLICATIONS

This invention is related to commonly assigned U.S. patent application Ser. Nos. 839,701 filed Oct. 5, 1977 in the name of M. J. Esper et al and entitled "Catalytic Material Impregnated Porous Variably Resistive Exhaust Gas Sensor and Method of Impregnation", now abandoned, and 839,704 filed Oct. 5, 1977 in the name of M. J. Cermak et al and entitled "Temperature Compensated Resistive Exhaust Gas Sensor Construction", now U.S. Pat. No. 4,151,503.

BACKGROUND OF THE INVENTION

This invention relates to an improved sensor of the type having a ceramic element that undergoes a change in an electrical characteristic in response to a change in the partial pressure of oxygen in a mixture of gases to which the ceramic element is exposed. The ceramic element of the sensor may be either titania or zirconia under the current state of development, but other electrically responsive ceramics are known and may be used in the future. The preferred titania ceramic element is porous to provide a large surface area for effecting the transfer of oxygen from the titania to the gases to which the ceramic element is exposed and vice versa. The titania ceramic element has a porous or discontinuous coating of a precious metal charge transfer material. This material in the past has been platinum applied to the titania ceramic element by immersion in a solution containing platinum.

Sensors of the type having a zirconia ceramic element also utilize a porous platinum charge transfer material, but the zirconia ceramic is very dense and the platinum is applied to the zirconia surfaces by vapor deposition. The surface platinum to be exposed to engine exhaust gases is usually covered with a porous refractory material to aid in bonding and for the protection of the platinum.

Sensors of the type discussed above are particularly suited for use in detecting excursions, above and below stoichiometry, of the air-fuel ratio of the mixture of air and fuel supplied to an internal combustion engine. In accomplishing this detection, the sensor is positioned in the path of the exhaust gases emanating from the engine. As the mixture supplied to the engine changes from rich to lean, the exhaust gases change from a composition including very little oxygen to a composition containing an excess of oxygen. As the exhaust gases change from lean to rich, the reverse changes in composition occur. The sensors have an electrical characteristic that undergoes a step-function change as a result of the mixture excursions across the stoichiometric air-fuel ratio.

The titania ceramic material undergoes a change in its resistance as a function of the oxygen concentration gradient between the titania and the exhaust gases. The zirconia ceramic element undergoes a change in the EMF produced across its platinum change transfer electrodes as a function of the oxygen concentration differential on opposite sides of the zirconia material. With the zirconia sensor, a reference gas, usually air, is applied to one side of the zirconia and the exhaust gas composition is allowed to contact the other side of the zirconia. The use of a reference gas is unnecessary in connection with titania sensors, and the entire titania ceramic element is immersed in the exhaust gases.

The present invention is particularly directed to a titania sensor, but has possible application to zirconia sensors and others if problems peculiar to these sensors are eliminated or become less extreme as the art progresses.

The specific problem solved by the present invention is the loss of response to air-fuel mixture variations that occurs with the prior art titania sensor as a result of its use over a relatively short period of time. This loss of response occurs in the lower portion of the normal operating temperature range, which extends from about 300° C. to about 900° C. The failure of the sensor to operate at low temperatures due to loss of its low temperature response is a very serious problem because it means that the feedback fuel control system associated with the sensor for controlling the mixture ratios supplied to an internal combustion engine cannot be operated until the exhaust gases have heated the sensor sufficiently to maintain its temperature above that at which it is able to respond to air-fuel ratio variations. These may increase undesirable engine exhaust emissions and reduce fuel economy during engine warm-up conditions.

SUMMARY OF THE INVENTION

The inventors have discovered that the porous or discontinuous platinum coating on the porous titania ceramic element forms an oxide, $PtO_2$, that vaporizes and that thereby is removed from the titania element when it is exposed to the higher temperatures within the aforementioned normal range of operating temperatures. These temperatures occur during normal sensor usage when the sensor is subjected to exhaust gases produced by lean mixtures having excess oxygen content. If the sensor temperature is at about 850° C. during this time, the platinum oxide forms, vaporizes, and is lost. While this may not adversely affect the operation of the sensor when being used under high temperature conditions, it very adversely affects the sensor with respect to its low-temperature operability and response time. This can cause the forementioned deleterious effects on the fuel control system.

It has been found that the vaporization loss of the platinum charge transfer material applied to the titania ceramic element of an exhaust gas sensor can be substantially eliminated. Also, the minimum operating temperature of the prior art titania sensor, even with its platinum charge transfer material intact, can be substantially reduced so that the sensor can be used earlier in the operation of a cold internal combustion engine to achieve closed-loop feedback air-fuel ratio control. This is achieved by the application to the titania oxygen-sensing element of an alloy of platinum and at least one other metal which has a lower ionization potential and vapor pressure than platinum and that forms an oxide that is more stable in the normal operating temperature range of the sensor than is the oxide of platinum. More specifically, it has been found that a charge transfer material that comprises an alloy of platinum and rhodium may be used to achieve the benefits described above. Preferably, the alloy is comprised by weight of nine parts of platinum for each part of rhodium.

The elimination of the prior art problem and the additional advantages of the invention are obtained without degradation in the response time of the sensor. The sensor improvement is brought about by the addition of rhodium, which forms an oxide (RhO$_2$) at elevated temperatures that is considerably more stable than is the oxide of platinum and increases the life of the charge transfer material.

The greater the stability of the oxide of the charge transfer material, the longer one would expect the sensor response time to be due to the lower electrical conductivity of the metal oxide and the interference of the oxide with oxygen transfer from and to the titania crystal structure. Pure platinum would be expected to facilitate rapid transfer of oxygen from the ceramic element to the exhaust gases and vice versa and, therefore, platinum in its pure form would be the optimum metal for a titania sensor charge transfer material. Unfortunately, the inventors have found that the high vapor pressure of platinum and its oxide is responsible for its loss from the titania element during operation of the sensor above about 850° C. Of course, if the titania sensor is not to be operated at temperatures and conditions at which platinum oxide is formed, then pure platinum or some other electrically conductive material may be the "optimum" charge transfer material for such application. The charge transfer material is an electrical conductor; it is not regarded as a catalyst because it does not promote chemical reaction of exhaust gas constituents in its activity related to variation of the ceramic electrical characteristic.

With a fresh sensor having a charge transfer material of pure platinum, the prior art sensor response time initially is very fast, but as a result of vaporization of the platinum or its oxide at elevated sensor operating temperatures, the response time at low operating temperatures degrades substantially. The addition of a metal, rhodium in particular, to the platinum has been found to prevent the rapid vaporization of the charge transfer material and allow the sensor to respond to variations in the oxygen content of gases to which the sensor is exposed at considerably lower operating temperatures than is characteristic of the prior art device.

The invention may be better understood by reference to the detailed description which follows and to the drawings.

BRIEF DESCRIPTION OF THE DRAWINGS

FIG. 9 is a graph illustrating the voltage response of the titania sensor as a function of time with an air-fuel ratio that varies by about 0.1 ratios above and below stoichiometry;

DETAILED DESCRIPTION

Figures 1, 2:
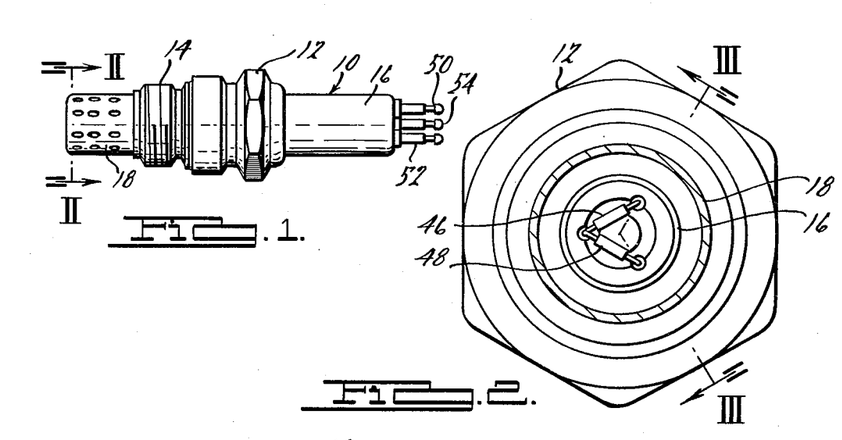
FIG. 1 is an elevational view of a titania exhaust gas oxygen sensor suitable for installation in the intake manifold of an external combustion engine.
FIG. 2 is a sectional end view, taken along the line II—II in FIG. 1, of the sensor of FIG. 1 and is shown in enlarged scale.
Figure 3:
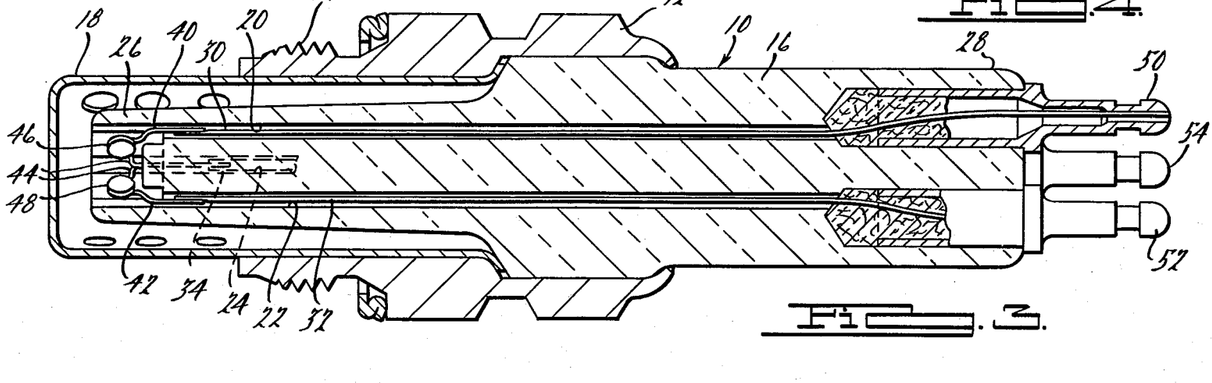
FIG. 3 is a sectional view, taken along the line III—III in FIG. 2, showing the internal structure of the sensor of FIGS. 1 and 2 also on an enlarged scale.

With particular reference now to FIGS. 1 through 3, wherein like numerals refer to like parts in the several views, there is shown a complete titania exhaust gas sensor assembly generally designated by the numeral 10. The sensor 10 includes a steel housing or body 12, which may be substantially identical to a typical spark plug body, having a threaded portion 14 for engagement with a suitably threaded aperture provided within the exhaust system of an internal combustion engine (not shown). In most cases, the sensor 10 would be installed in an aperture at a location in the exhaust manifold near the flange that would connect to an exhaust pipe. A ceramic insulator 16 extends through the body 12 and has a tapered portion 26 projecting outwardly from the body 12 into the volume defined by the boundaries of a perforated shield 18. There are three longitudinal passages 20, 22 and 24 extending from the projecting end 26 of the ceramic insulator to its opposite end 28. Wires 30, 32 and 34 are located in the respectively corresponding passages 20, 22 and 24 and are of a heat resistant character, preferably being made from an alloy such as 80% nickel-20% chromium wire. These electrically conductive wires are welded to precious-metal wire leads 40, 42 and 44, which are embedded in disc-shaped ceramic elements 46 and 48.

Element 46 is a ceramic titania O$_2$ sensor responsive to the partial pressure of oxygen in the gaseous medium to which this element is exposed. Sensor element 46 may be fabricated in accordance with the teachings of commonly assigned U.S. Pat. Nos. 3,886,785 issued June 3, 1975 and 3,932,246 issued Jan. 13, 1976, both in the names of Stadler et al. The teachings of the present invention must, however, also be considered in the fabrication of the oxygen sensing element 46. The present invention teaches the application to the porous oxygen sensor of a platinum alloy (atomic or fine particle mixture) charge transfer material for reasons which are hereinafter made clear.

The element 48 is a thermistor. The thermistor may be made from titania ceramic material of greater density, near its theoretical density, than the density of the porous titania oxygen sensor 46. Alternatively, the thermistor 48 may be constructed in accordance with the teachings of copending and commonly assigned U.S. Patent application Ser. No. 857,498 filed Dec. 5, 1977 in the names of Logothetis, Laud and Park and entitled "Rare Earth—Yttrium, transition metal oxide Thermistors", now U.S. Pat. No. 4,162,431. The thermistor 48 is intended to provide temperature compensation in accordance with the circuitry illustrated in FIG. 4 and is intended to be substantially nonresponsive to variations in the partial pressure of oxygen in the gaseous medium to which it is exposed.

The sensor of FIGS. 1 through 3 is intended to be used in conjunction with electronic circuitry for closed-loop feedback control of the amount of fuel supplied to an internal combustion engine. The sensor indicates whether the exhaust gases contain a substantial amount of HC and CO or whether instead there is a substantial amount of oxygen, thereby, indicating whether or not the air-fuel ratio of the mixture supplied to the engine was rich or lean with respect to the stoichiometric value of about 14.7 parts of air to each part of fuel by weight. This air-fuel ratio typically is expressed as a normalized air-fuel ratio lambda, wherein the actual ratio is divided by the stoichiometric value and the stoichiometric ratio therefore is represented as 1.0 in accordance with well known practice.

Figure 4:
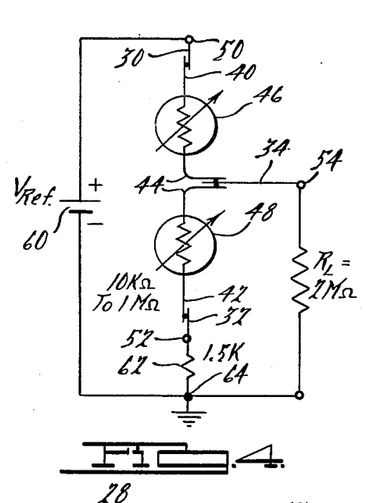
FIG. 4 is a circuit diagram illustrating the manner in which the titania oxygen sensing element and the thermistor shown in FIGS. 1 through 3 are electrically connected with circuitry designed to receive the sensor output voltage.

The exhaust gas sensor 10 has terminals 50, 52 and 54 designed for connection to external circuitry as specified above to enable it to be used in a feedback fuel control system. With particular reference now to FIG. 4, there is shown a circuit that schematically represents the manner in which the sensor 10 is utilized in association with such external circuitry. A DC source of regulated reference voltage 60 has its positive terminal connected to terminal 50 of the sensor oxygen responsive element 46. The lead wires 40, 42 and 44 from the sensor 46 and thermistor 48 are welded or otherwise joined, respectively, to lead wires 30, 32 and 34 to interconnect the two ceramic elements 46 and 48 as shown. The thermistor element 48 is connected through a response-shaping resistor 62 to ground potential at 64. The output voltage of the sensor 10 is taken between the sensor terminal 54 and ground potential. This signal is applied across the input impedance or load resistance $R_L$ (about two megohms) of the engine control electronic circuitry.

The input voltage to the circuit of FIG. 4 is obtained from the source reference 60 and is applied across the voltage divider comprising the series-connected variable resistances of oxygen sensor 46 and thermistor 48 is series with the response-shaping resistor 62. The output voltage is taken across the load resistance $R_L$.

The resistance values of both the oxygen sensor 46 and the thermistor 48 vary as a function of temperature and in the same direction, that is, the resistance of these elements decreases with increasing temperature. As a result, the voltage dividing effect provides an output voltage across the load resistance $R_L$ that is independent of temperature. The oxygen sensor 46, however, has a resistance which varies not only with temperature but also with the partial pressure of oxygen in the gaseous medium to which the sensor is exposed. An increase in the resistance of the oxygen sensor 46 causes the output voltage across the load $R_L$ to decrease, and a reduction in the resistance of the oxygen sensor causes a corresponding increase in the output voltage across the resistance $R_L$. Otherwise stated, an increase in oxygen content in the gaseous medium surrounding the oxygen sensing device 46 causes its resistance to increase in a manner hereinafter described and thereby causes a reduction in the voltage across the load resistance $R_L$. A decrease in the oxygen content of the gaseous medium causes the resistance of the oxygen sensor 46 to decrease in a corresponding manner and this causes an increase in the voltage across the load resistance $R_L$.

Figure 5:
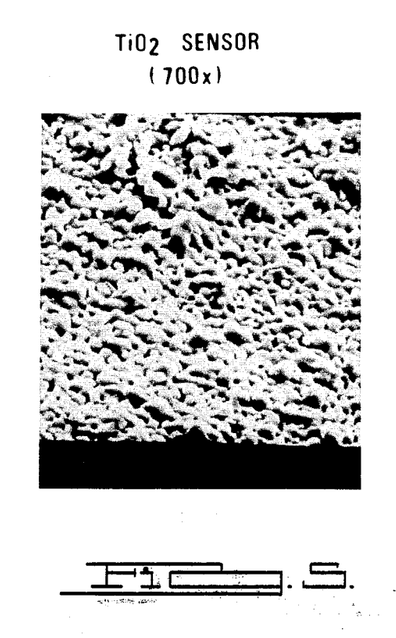
FIGS. 5 and 6 are photomicrographs of the titania oxygen sensor and the thermistor illustrated in FIGS. 1 through 4.
Figure 6:
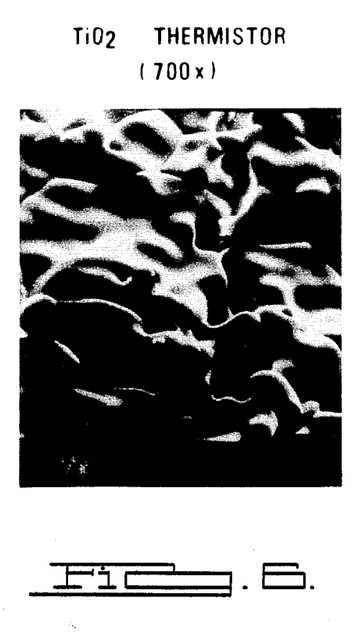

FIG. 5 is a photomicrograph of the titania oxygen sensor 46 with a magnification of 700 times size. FIG. 6 is a photomicrograph of a titania thermistor 48 with a similar magnification of 700 times size. From the FIG. 5 titania sensor photomicrograph, it may be seen quite clearly that the oxygen sensor structure is very porous. Also, its grain size is very small as compared to the much larger grain size of the titania thermistor, which is much more dense and which lacks the porosity of the titania oxygen sensor.

Titanium dioxide (titania) is a material that occurs naturally in mixture with other minerals. The titania is obtained by precipitation from a solution of minerals that include titania. When thus obtained by precipitation, the titania has an anatase crystal structure. When the titania material in this crystal structure is formed into an exhaust gas oxygen sensor, it is first thermally treated in a manner that allows the crystal structure to change from anatase to rutile. An increase in the temperature of the rutile material above room temperature induces oxygen vacancies into the crystal structure. This results in ionization of the titanium atoms interstitially located in the crystal structure. The concentration of the interstitial titanium ions and oxygen vacancies increase as temperature rises, and these variations in concentration are of considerable significance in the use of titania as a sensor material.

Figure 7:
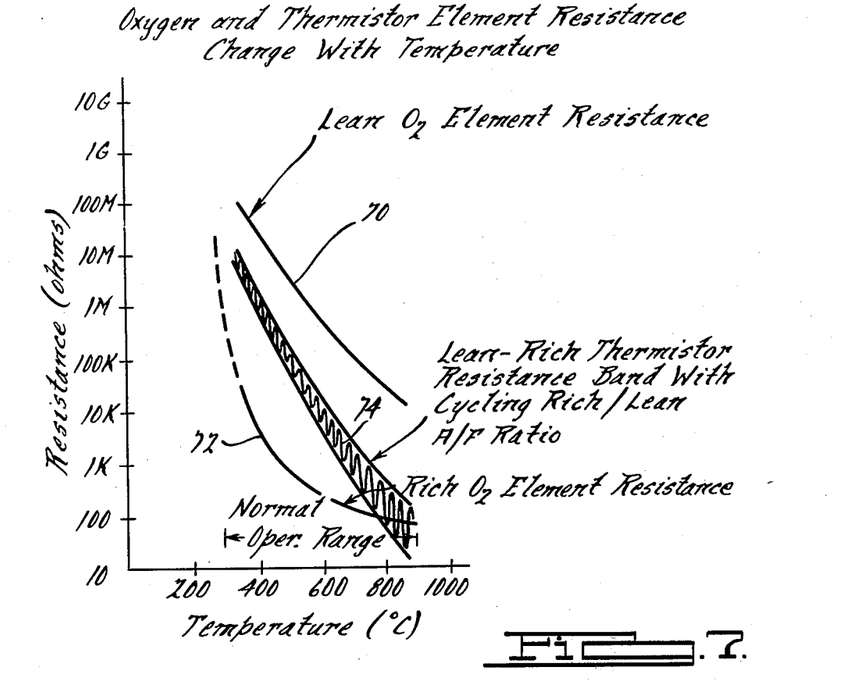
FIG. 7 is a graph of both the oxygen sensor element and thermistor element resistance as a function of temperature over the normal operating range from about 300° C. to about 900° C.

FIG. 7 illustrates the manner in which the resistance of the oxygen sensing element 46 and the thermistor element 48 vary as a function of temperature. Curve 70 represents the resistance of the oxygen sensor when it is located in the exhaust gas emanating from an internal combustion engine supplied with a lean air-fuel mixture, that is, a mixture that has a quantity of oxygen greater than that required for stoichiometric combustion. The curve 72 represents the resistance of that sensor when located in the exhaust gases emanating from an engine supplied with a rich mixture. Curve 74 illustrates the resistance of the thermistor 48 as a function of temperature. The curve is of alternating character indicating the small variation of the thermistor resistance that occurs as the air-fuel ratio supplied to the engine oscillates back and forth about stoichiometry. From curve 74, it is quite evident that there is but very minor variation in the resistance of the thermistor 48 as a function of the oxygen content in the gaseous medium surrounding the sensor. This is much in contrast to the curves 70 and 72 representing, respectively, the lean and rich resistance values over the normal operating range of exhaust gas sensor 10. Of course, the actual resistance values for the oxygen sensor element 46 would vary back and forth between the curves 70 and 72 as the air-fuel ratio supplied to the engine was varied about stoichiometry. At the left side of the graph of FIG. 7, it may be seen that the curves 70 and 72 come together at low temperatures. This indicates that titania is not responsive to the surrounding oxygen concentration at low temperatures.

A very significant feature of the present invention is that the portion of the curves 70 and 72 at which the sensor becomes responsive to oxygen concentration occurs at a lower temperature than with the prior art device. This feature, together with elimination of the degradation in low temperature response experienced in the prior art device, are very substantial benefits.

The fact that rutile titania, as previously described, has deficiencies where atoms of oxygen are missing is responsible for much of the resistance variation indicated in FIG. 7.

If it is assumed that a titania sensor, such as sensor element 46, is located in an environment in which the oxygen concentration is constant and only the temperature varies, then the number of vacancies in the titania structure may change due to thermal energy. However, the titanium atom in those titanium oxide molecules having but one oxygen atom, have only two of their four valence electrons covalently bonded with oxygen. As the temperature of the titania increases, the thermal energy supplied to the molecules in the structure increases and the oxygen vacancies therein have greater mobility. As the oxygen deficiency and concentration of Ti interstitials increases, more electrons become available for the conduction process, and the resistivity of the material decreases. The conductivity of the titania increases or, otherwise stated, its resistance decreases as a function of temperature, as is indicated in FIG. 7 for both the thermistor and oxygen sensor element.

If it is now assumed that a sensor element 46 of titania is positioned in an environment of varying oxygen partial pressure and that it is at a temperature within the titania operating range, for example, 600° C., then the number of vacancies in titania increases or decreases as a function of oxygen partial pressure.

If a titania oxygen sensor 46 is positioned in the exhaust stream of an internal combustion engine and if the air-fuel mixture supplied to such engine continually varies between lean and rich with rexpect to stoichiometry, the partial pressure of oxygen to which the sensor is exposed varies cyclically. When the mixture is lean, there is an excess of oxygen in the exhaust gas and few oxidizable carbon compounds. The titania element has a relatively high resistance, on the order of about 0.05 megohms. This is because oxygen from the exhaust gases will have been adsorbed on the surface of the titania element. The adsorbed oxygen atoms on the titania surface annihilate oxygen vacancies and interstitial titanium ions and migrate into the titania crystal structure. In an oxygen deficient oxide, both oxygen vacancies and interstitial ions may be involved in an equilibrium reaction with oxygen in the surrounding environment. In this equilibrium reaction, the partial pressure of oxygen in the environment determines whether the interstitial ions or the oxygen vacancies play the predominant role in the oxygen transfer process. In both cases, there is an acquisition of electrons followed by an annihilation of a vacancy and an interstitial ion. The electrons at low sensor operating temperatures are provided by the charge transfer material, which is an electrical conductor having a "pool" of available electrons. At higher temperatures, thermal energy is sufficient to provide electrons required at the titania surface for the process of vacancy annihilation.

The lower the number of vacancies in the titania crystal structure, the higher is its electrical resistance. On the other hand, the more vacancies that are created in the crystal structure, the lower is the titania resistance.

When the exhaust gases change from lean-to-rich (L-R), a percentage of the oxygen atoms in the titania structure are removed to create additional vacancies. The oxygen leaves the titania crystal structure probably as a negatively charged ion. As a result, there is a positively charged vacancy left behind. At the titania surface, either the oxygen ion reacts with an oxidizable carbon compound in the exhaust gas or two oxygen atoms or ions unite to form an oxygen molecule.

When the exhaust gases change to a composition corresponding to a lean mixture, the concentration of oxidizable carbon compounds is drastically reduced and an excess of oxygen appears in the exhaust gas. The oxygen concentration gradient reverses, and oxygen atoms are adsorbed on the titania surface and fill vacancies therein as was previously mentioned.

Figure 8:
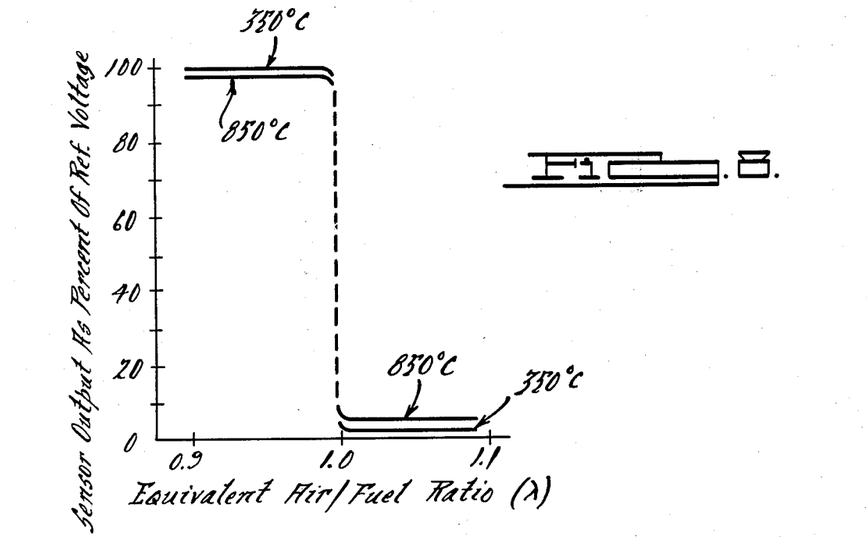
FIG. 8 is a graph of sensor output voltage as a percent of the input (reference) voltage versus equivalent air-fuel ratio.

FIG. 8 illustrates the manner in which the output voltage of the sensor 10, connected in the circuit of FIG. 4, varies as a function of air-fuel ratio where this ratio changes from rich (below 14.7) to lean (above 14.7). When the mixture is rich, the sensor element 46 has a low resistance and the sensor output voltage is almost 100 percent, the percentage figure being the ratio of the actual output voltage to the input reference voltage multiplied by 100 percent. It may be seen that, with the temperature compensation provided by the thermistor 48, there is very little variation in the sensor output voltage as a function of variation in temperature between 350° C. and 850° C. Under rich conditions, the removal of oxygen from the titania structure to create new vacancies provides additional electrons from the titanium atoms that may be used for the purpose of conduction. This explains the greatly increased conductivity of titania when exposed to exhaust gases produced by the combustion of rich mixtures. The opposite effect explains the very high resistance and low conductivity of the titania sensor element when exposed to exhaust gases produced by lean mixtures.

In the aforementioned U.S. Patent Application Ser. No. 839,701, entitled "Catalytic Material Impregnated Porous Variably Resistive Exhaust Gas Sensor and Method of Impregnation", there is described the use of a "catalyst" of platinum on the surface of the titania sensor element 46. The platinum is dispersed throughout the porous titania element for the purpose of enhancing its response characteristics at low temperatures.

The use of the term "catalyst" to describe the metallic platinum deposited on the titania element is believed to be a misnomer; little or no catalytic action is believed to take place. The metal on the titania functions as a charge transfer material to promote, particularly at the lower portion of the sensor operating range, the acquisition and removal of oxygen from the titania crystal structure as a result of air-fuel changes from rich-to-lean and lean-to-rich, respectively. The metal is very thin and may be located at or near the grain boundaries of the titania and is preferably discontinuous to facilitate the acquisition and removal of oxygen from the titania.

FIG. 9 illustrates the actual output-voltage response of a titania exhaust gas sensor exposed to exhaust gases produced by both rich and lean mixtures where these mixtures cycled between rich and lean once each second. The sensor response time is defined as the time required for the sensor to traverse from 33% to 66% of the reference voltage when the air-fuel ratio changes from lean to rich and the time required for the sensor to traverse from 66% to 33% of the reference voltage when the air-fuel ratio changes from rich to lean. The sensor response depicted in FIG. 9 is taken from an output-voltage trace of a titania sensor. The trace was obtained during a test conducted with a vapor-carburetor facility. During the test, air-fuel ratio was modulated in a step-function manner with ±1.5 air-fuel ratio variation about the stoichiometric value. Response time is fast, on the order of 10 to 20 milliseconds, and these very low values are difficult to measure.

With respect to sensors manufactured in accordance with the teachings of the aforementioned U.S. Patent application Ser. No. 839,701, the platinum charge transfer material applied to the porous titania oxygen sensor element was found to substantially improve the sensor response time as compared to a titania oxygen sensor having no charge transfer material, particularly at low sensor operating temperatures. Unfortunately, it was found that the sensors having platinum as a charge transfer material developed substantially lengthened response times after the sensors had been in use for a number of hours. Not only did the response time become very slow for these sensors, but also the minimum temperature at which the sensor output response occurs increased substantially. This was very undesirable. The sensor should respond at as low a temperature as possible so that feedback fuel control of the air-fuel ratio supplied to the internal combustion engine may be achieved at an early stage during its warm-up period.

The inventors have discovered that the change in response time of the sensor and the increased minimum operating temperature are the result of loss of the platinum charge transfer material that had been deposited on the titania sensor element. This loss is the result of the oxidation of the platinum at the higher sensor operating temperatures normally encountered. Platinum forms platinum oxide $PtO_2$ at elevated temperatures, with substantial amounts being formed at about 850° C. Unfortunately, platinum oxide vaporizes quite readily and leaves the porous titania oxygen sensing element 46. In a cooler portion of the exhaust conduit, the platinum oxide decomposes and is deposited as pure platinum. In fact, it has been found that some of the platinum is deposited on the nearby thermistor 48, which tends to be somewhat cooler than the oxygen sensor 46. This adversely affects the behavior of the thermistor by increasing its response to variations in the partial pressure of oxygen in the exhaust gas. The thermistor is intended to respond only to temperature.

The inventors have found that if a small amount of rhodium is added to the platinum charge transfer material, not only can the vaporization of the charge transfer material be prevented, but the response time of the sensor can be made very fast, about equal to that of a fresh titania sensor with a platinum charge transfer material. Also, the minimum operating temperature of the sensor can be substantially reduced below the minimum operating temperature of a titania sensor having pure platinum as the charge transfer material. An important characteristic of the improvement is that a small amount of rhodium, a material which has a lower vaporization pressure than platinum and which has a lower ionization potential as well, provides the enhanced sensor behavior.

A solution of platinum and rhodium in 2½% concentration may be used to apply the platinum/rhodium charge transfer material to a porous titania sensor element 46. Solution containing nine parts by weight platinum to one part by weight rhodium (a 90/10 platinum-rhodium composition) is believed to be very satisfactory in achieving the results described herein. A solution containing platinum in the above ratio and in the amount of 2½% by weight is formed by mixture of chloroplatinic acid and rhodium chloride. The platinum and rhodium ions in the solution are intimately mixed on an atomic scale. A fresh titania sensor element is immersed in the solution. The solution then is allowed to evaporate leaving crystals of platinum chloride and rhodium chloride on the sensor element. It is believed that these crystals are very fine and are so intimately mixed that, upon heating of the titania sensor element to about 900° C., the salts decompose to leave platinum and rhodium atoms mixed with one another on an atomic scale. Thus, it is believed that a true alloy of platinum and rhodium is formed by use of the above procedure. This platinum/rhodium alloy forms the charge transfer material for titania that produces the results hereinafter described.

Figure 10:
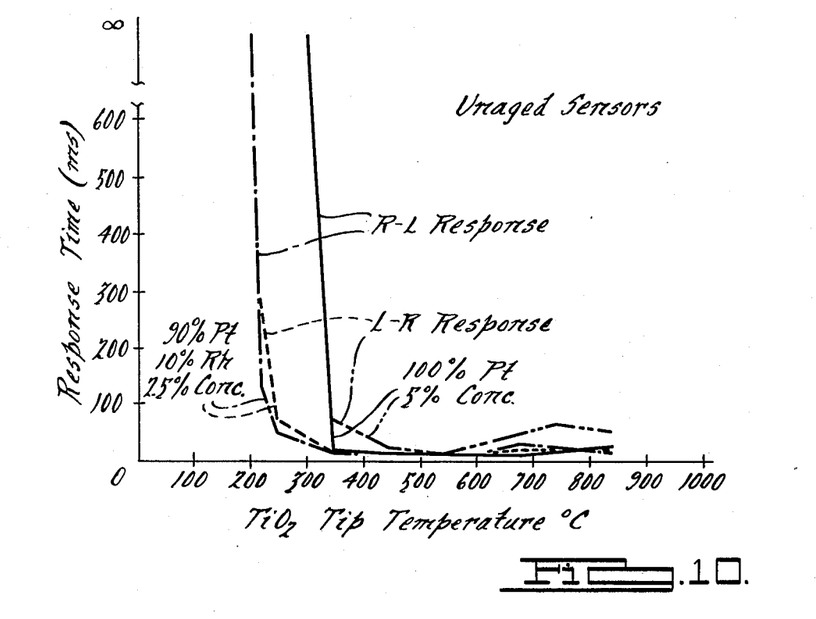
FIG. 10 is a graph of the response time of unaged titania sensors versus the sensor tip temperature for both Pt and Pt/Rh charge transfer materials.

With particular reference to FIG. 10, there is shown a comparison of the response time of unaged (fresh) titania oxygen sensors as a function of titania element tip temperature in °C. Temperatures are measured with a thermocouple positioned between, but not quite in contact with, the oxygen sensing element 46 and the thermistor 48. The data is plotted for rich-to-lean and lean-to-rich responses of some sensor elements having 100% platinum deposited by solution thereon as described in the aforementioned U.S. Patent application Ser. No. 839,701 and other sensor elements having the platinum/rhodium alloy of the present invention deposited thereon as taught herein.

Each data point in this graph represents the average of the response times of twenty-three sensors. The R-L response time of fresh sensors having a pure Pt charge transfer material applied in a 5% solution of chloroplatinic acid ($H_2PtCl_6$) may be seen to go from infinity to about 30 msec in the 300° C. temperature range. The L-R response time for this group of sensors having Pt charge transfer material is essentially identical to the R-L response, except where the respective curves diverge at the temperature region of about 330° C.

Also represented in FIG. 10 is a group of sensors having a charge transfer material of 90% Pt and 10% Rh applied to the porous titania in a solution of $H_2PtCl_6$ and $RhCl_3.3H_2O$ containing Pt and Rh in total amount of 2½% by weight. Both the R-L and L-R response times for this group are illustrated. These response times go from infinity to less than 50 msec over the temperature range from about 200° to 275° C.

As previously mentioned, all of the data for FIG. 10 was obtained from fresh (unaged) titania sensors. It is evident that the use of the 90% Pt/10% Rh charge transfer material has substantially reduced the minimum operating temperature of the fresh titania sensors while also providing the same fast response time over the entire normal sensor operating range as the sensors with pure Pt charge transfer material.

Figure 11:
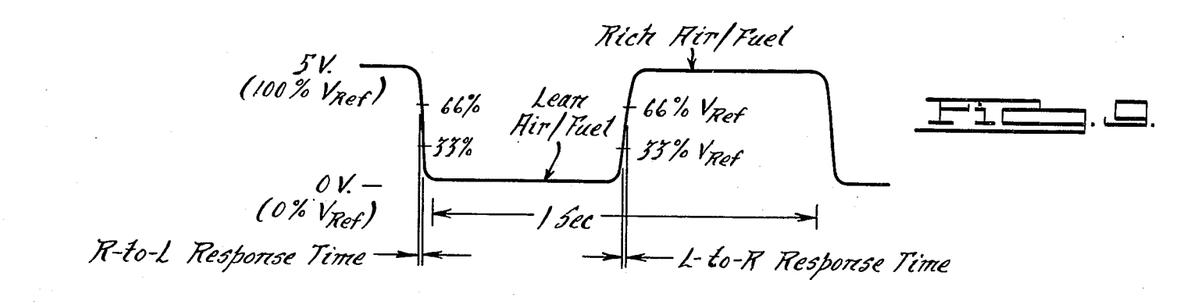
FIG. 11 is a graph of the response time of an aged sensor versus the sensor tip temperature for both Pt and Pt/Rh charge transfer materials.

FIG. 11 is similar to FIG. 10, but shows results obtained for the twenty-three sensors after they had been exposed, for 250 hours, to the exhaust gases produced by the combustion of a natural gas/air mixture that varied cyclically each second about the stoichiometric mixture level. The data establishes some degradation in response time for sensors having either the pure Pt or the 90% Pt/10% Rh charge transfer materials. However, the substantial improvement obtained from the Pt/Rh charge transfer material on fresh sensors is retained after the 250 hours of aging. The minimum operating temperature is down to about 250° C. for the Pt/Rh sensors and is about 400° C. for the Pt sensors. The time response over the entire normal operating temperature range is very satisfactory for the Pt/Rh sensors. The shift to a minimum operating temperature of 400° C. for the Pt sensor group is caused by vaporization loss of the Pt charge transfer material.

Figure 12:
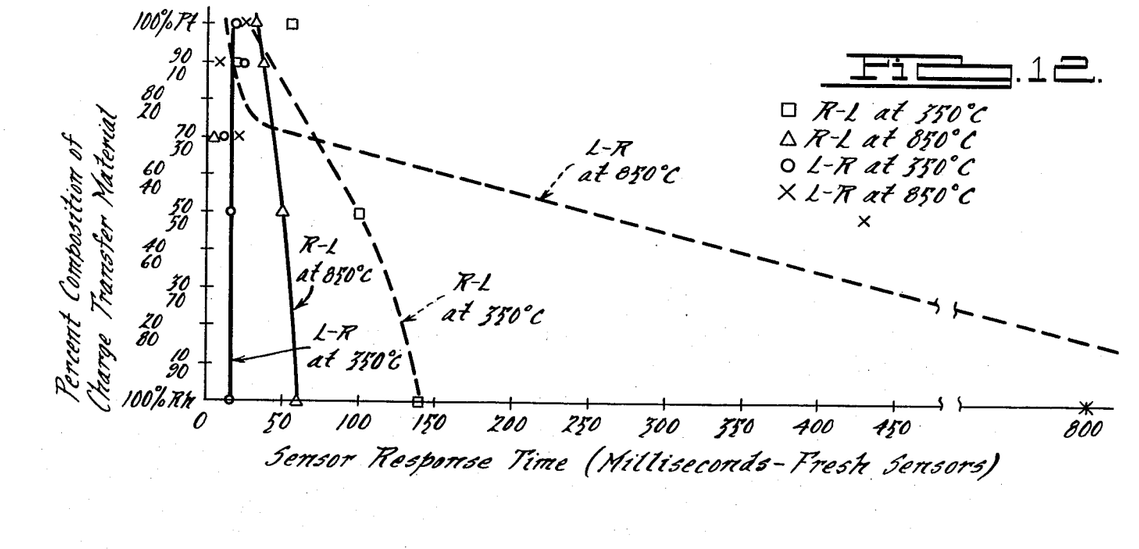
FIG. 12 is a graph of titania sensor response time as a function of the percent composition of the charge transfer material on the titania oxygen sensor element.

FIG. 12 is a graph of percent Pt-Rh composition versus sensor response time. The plotted data points for Pt-Rh alloys each are the average of data obtained from measurements made on six fresh sensors. Otherwise stated, there were six sensors having a 100% Rh charge transfer material, six sensors having a 50% Pt/50% Rh charge transfer material, six sensors having a 70% Pt/30% Rh charge transfer material, and six sensors having a 90% Pt/10% Rh charge transfer material. The data for sensors having 100% Pt charge transfer material was obtained from a group of fresh sensors.

In FIG. 12, curves are provided for R-L response time at 350° C., for L-R response time at 350° C., for R-L response time at 850° C. and for L-R response time at 850° C. The L-R response time at the lower operating temperature of 350° C. is independent of the percent Pt/Rh composition. On the other hand, the R-L response times at both 350° C. and the higher 850° C. temperature increase as the %Rh in the charge transfer material is increased. In other words, it appears that Rh in the charge transfer material degrades the sensor performance by increasing the response time of the fresh sensors, particularly at 350° C. in the lower portion of the normal sensor operating temperature range.

The effect of increasing Rh content in the Pt/Rh charge transfer material is especially pronounced with respect to the L-R response time at 850° C.

From the data plotted in FIG. 12, it is clear that for Pt/Rh charge transfer materials in the range of compositions from 70% Pt/30% Rh to 100% Pt/0% Rh, there is little if any degradation in the response time of the sensors. On the other hand, the L-R response at 850° C. for compositional ranges between 70% Pt/30% Rh and 0% Pt/100% Rh is very much affected by the increasing rhodium content. The reason for this is described in the following paragraph.

At higher temperatures in a lean exhaust gas environment, the titania sensor having both Pt and Rh mixed together in the charge transfer material forms oxides of both Pt and Rh. The Pt oxide ($PtO_2$) is less stable than the Rh oxide ($RhO_2$). When the mixture changes from L-R so that there is substantially less oxygen in the gaseous exhaust mixture, then oxygen is removed from the titania sensor and from the charge transfer material. The Pt oxide breaks down easily and its oxygen is removed quite rapidly, but the Rh oxide is more stable than the Pt oxide and it takes longer to decompose into oxygen and rhodium. The presence of the Rh oxide delays the removal of oxygen from the titania crystal structure and therefore delays a reduction in its resistance. The more Rh there is present in the charge transfer material, the slower is the titania sensor response, as is demonstrated by the L-R curve at 850° C. in FIG. 12. However, as shown by FIG. 12, for compositions of the charge transfer material having 30% or less Rh by weight, there is little if any degradation in response time, but yet this small amount of Rh is sufficient to prevent vaporization of the oxidized charge transfer material. This is believed to be because Rh has a lower vapor pressure than does platinum and the platinum/rhodium alloy also has a lower vapor pressure than pure Pt. This prevents loss of the oxidized charge transfer material at elevated normal operating temperatures, in contrast to the vaporization loss which occurs where the charge transfer material is pure Pt.

Figure 13:
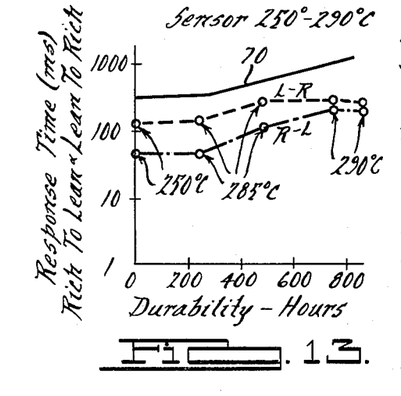
FIGS. 13 through 18 are graphs that illustrate the response time and voltage characteristics of the improved titania sensors at different operating temperatures during and after durability testing to 850 hours on an engine dynamometer.
Figure 14:
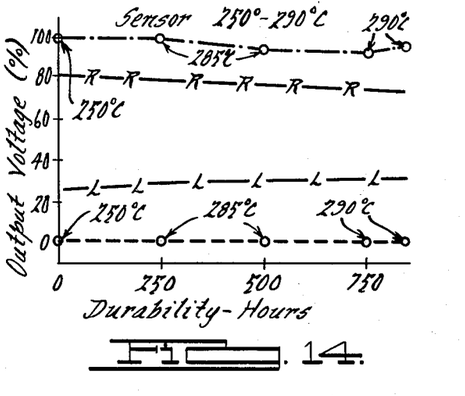
Figure 15:
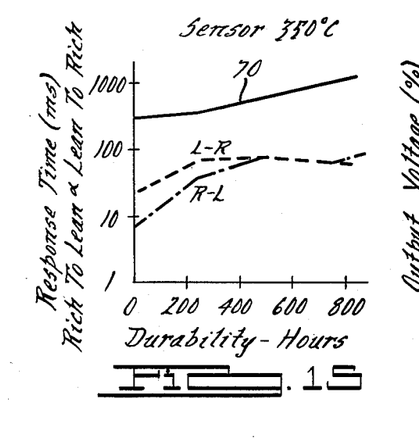
Figure 16:
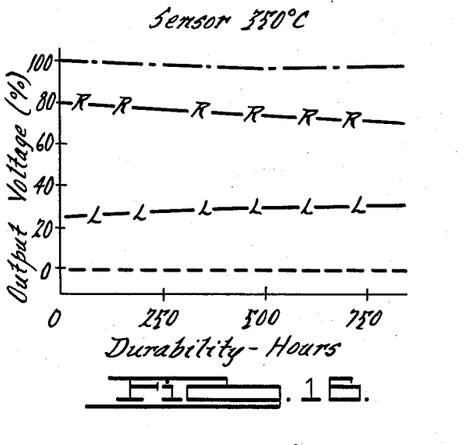
Figure 17:
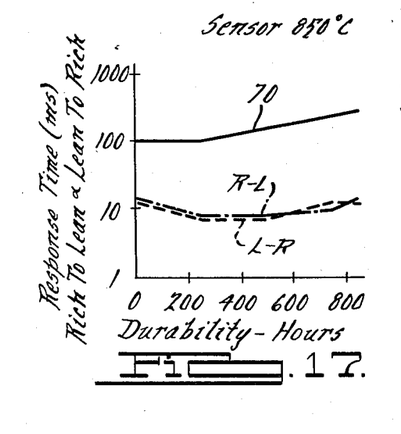
Figure 18:
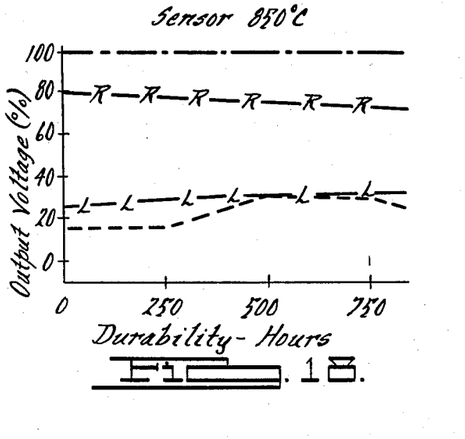

FIGS. 13 through 18 graphically depict, for specified sensor operating temperatures, the durability of the sensors having Pt/Rh charge transfer material applied as taught herein. The solid lines 70 in FIGS. 13, 15 and 17 represent the maximum permissible response time for exhaust gas sensors as currently specified by Ford Motor Company. In FIGS. 14, 16 and 18, the broken lines having the letters R and L depict, respectively, the rich minimum and lean maximum output voltage specified by Ford Motor Company for exhaust gas sensors in use over a period of hours.

The data for FIGS. 13 through 18 was obtained from titania exhaust gas sensors having Pt/Rh charge transfer materials applied in a 2.5% by weight solution wherein the ratio of Pt to Rh was nine parts Pt to one part Rh. The titania exhaust gas sensors were used on a feedback carburetor engine of 2.3 liter displacement. The values depicted are for 25 sensors tested for durability on a dynamometer. FIGS. 13, 15 and 17 show response times, both R-L and L-R for these sensors as a function of durability in hours. FIGS. 14, 16 and 18 show the output voltage of these sensors (percent of the input reference voltage) as a function of durability hours.

In FIGS. 13 and 14, it may be seen that the lean-to-rich and rich-to-lean response times for these sensors remain below the specification limit for 350° C. over the entire durability time of 850 hours where the sensor tip temperature was between 250° and 290° C. Specific temperatures are indicated for all of the data points in FIG. 13. FIG. 14 shows that the rich and lean output voltages were substantially above the minimum-for-rich and below the maximum-for-lean specification limits for sensor temperatures from 250° to 290° C.

FIGS. 15 and 16 show the durability of the sensors when operated at a sensor tip temperature of 350° C. Again it may be seen that the response time for the sensors is below the specification limit for 350° C. and that the output voltages for rich are above the rich voltage specification minimum and for lean are below the lean maximum voltage limit.

FIGS. 17 and 18 show that, for operation of the sensor at 850° C., the response time is below the specification limit applicable thereto and the output voltages are above the minimum voltage limit for the rich condition and below the maximum voltage limit for the lean condition.

Zirconia exhaust gas sensors are known in the prior art. These sensors are ionically conductive, in contrast to the titania sensors which have a variable resistance electrical characteristic as has been described in detail herein. The zirconia sensor, however, is a device that utilizes a charge transfer material in the production of an EMF having a magnitude proportional to the log of the ratio of the respective partial pressures of oxygen applied to opposite sides of the zirconia ceramic material. This EMF is produced due to a difference in the oxygen concentrations on opposite sides of this ceramic material. Where there is such a difference, the side of the material having the greater oxygen concentration has oxygen molecules that are disassociated into oxygen atoms that pick up two electrons at the charge transfer material and thus becomes ions. The oxygen ions migrate through the zirconia ceramic material to the opposite side thereof. On this opposite side, there is another charge transfer material to which the oxygen ion gives up the two electrons previously picked up. In so doing, oxygen molecules again are formed, but there is an excess of negative charges on the side of the zirconia sensor to which the oxygen ion has migrated and then given up its charge. On the opposite side, the charge transfer material will have lost electrons and as a result an EMF or potential difference can be sensed. The external sensing circuitry connecting the charge transfer materials on opposite sides of the zirconia ceramic provides a high impedance path for electron flow from one of the charge transfer materials to the other.

The charge transfer material typically used with zirconia sensors is pure Pt. The zirconia ceramic is very dense and the Pt does not adhere well to this material. For this reason and for the protection of the Pt, the Pt is covered with a refractory material. The refractory material prevents vaporization or other loss of the Pt.

If suitable adhesion of a Pt/Rh charge transfer material could be achieved on the zirconia sensor, then these charge transfer materials would be able to achieve the benefits of the invention described herein and the elimination of the refractory material on the charge transfer material may be possible.

Based upon the foregoing description of the invention, what is claimed is:

1. An improved sensor of the type having a ceramic element that undergoes a change in an electrical characteristic of the ceramic element in response to a change in the partial pressure of oxygen in a mixture of gases to which the ceramic element is exposed, the ceramic element having electrodes connected thereto in spaced apart relationship and extending from the ceramic element to permit the resistance between them to be sensed, the ceramic element being porous to permit oxygen in the gases to which the ceramic element is exposed to migrate into and out of its interior regions, and the ceramic element having a discontinuous or porous charge transfer material deposited thereon, wherein the improvement comprises: a majority of the charge transfer material by weight is Pt and wherein Rh is included in an amount sufficient to allow the charge transfer material to be retained on the ceramic element when the ceramic element is exposed to gaseous mixtures produced by lean-mixture combustion at ceramic element temperatures in excess of about 850° C.

2. An improved sensor according to claim 1, wherein the charge transfer material consists essentially of Pt and Rh, the Rh being present in an amount not exceeding about 30% by weight of the total weight of Pt and Rh.

3. An improved sensor according to claim 2, wherein the charge transfer material consists essentially of Pt and Rh in alloy ratio of about nine parts by weight Pt to one part by weight Rh.

4. An improved sensor according to claim 3, wherein the ceramic element is porous and wherein the Pt and Rh are applied in a $2\frac{1}{2}$% by weight solution to the porous ceramic element, the ceramic element being immersed in the solution.

5. An improved sensor according to claim 4, wherein said solution comprises a mixture of $H_2PtCl_6$ and $RhCl_3.3H_2O$.

* * * * *